United States Patent [19]

Warrin et al.

[11] Patent Number: 4,492,574
[45] Date of Patent: Jan. 8, 1985

[54] ULTRASONIC ENDODONTIC DENTAL APPARATUS

[75] Inventors: George E. Warrin, North Merrick; Rene J. Perdreaux, Brooklyn, both of N.Y.

[73] Assignee: Cavitron, Inc., Long Island, N.Y.

[21] Appl. No.: 485,421

[22] Filed: Apr. 15, 1983

[51] Int. Cl.³ .............................................. A61C 5/02
[52] U.S. Cl. ....................................................... 433/81
[58] Field of Search .................................... 433/81, 102

[56] References Cited

U.S. PATENT DOCUMENTS 3,930,173  12/1975  Banko ................................. 433/119
4,247,288   1/1981  Yoshii .................................. 433/81

Primary Examiner—Robert Peshock
Attorney, Agent, or Firm—Vorys Sater Seymour & Pease

[57] ABSTRACT

An ultrasonic endodontic dental handpiece has an elongated housing supporting a coil connected for establishing an alternating magnetic field, the housing having a cooling fluid inlet at one end and being open at the other for receiving and supporting a removable insert. The insert includes an elongated hollow body having one end adapted to be insertably mounted in the open end of the housing in fluid communication with the interior of the handpiece, and an elongated tool support assembly telescopingly received in the body. The tool support assembly includes an elongated shaft member having a vibrator rigidly mounted on one end in position to be vibrated by the electromagnetic field and a seal located between the body and shank outboard of the housing to prevent the flow of cooling liquid through the body past the seal. A cooling fluid outlet is provided in the body between the housing in the seal to permit cooling fluid to flow through the handpiece, and an irrigation fluid passage is provided in the shaft outboard of the housing to permit the flow of irrigation fluid along the shaft to the terminal end of the insert assembly. A mounting head on the end of the shaft supports an endodontic instrument to be vibrated by the vibrator, with the head including a fluid flow passage for discharging irrigation fluid longitudinally of the endodontic instrument. An improved irrigation fluid dispenser is connected to the apparatus for selectively delivering irrigation fluid under pressure to the mounting head.

14 Claims, 3 Drawing Figures

ULTRASONIC ENDODONTIC DENTAL APPARATUS

BACKGROUND OF THE INVENTION

1. Field of the Invention

This invention relates to ultrasonic endodontic dental apparatus, and more particularly to an improved endodontic tool holder and root canal irrigating apparatus adapted to be used with an ultrasonic dental handpiece for debriding root canals and for directing fluid solutions, including medicaments, along the endodontic instrument for irrigating and treating the root canal during use of the instrument.

2. Description of the Prior Art

Ultrasonic endodontic dental tools employed as cutting or cleaning tools in dental procedures are known in which a liquid, conventionally water, is flowed through the ultrasonically driven head, or handpiece, to cool the handpiece. Such cooling water may flow through the handpiece and be discharged from the tool supporting end in the direction of the tool tip to irrigate and cool the work area. One such ultrasonic device is disclosed, for example, in U.S. Pat. No. Re. 30,536 and the present invention is particularly well adapted for use in ultrasonic devices of the type disclosed in this prior patent, the disclosure of which is incorporated herein by reference and reference to which may be had for a more complete understanding of the construction and operation of such ultrasonic handpieces.

It has also been proposed to use ultrasonically vibrated endodontic files in the performance of root canal therapy by supporting the file for axial, or longitudinal ultrasonic vibrations, and mounting the file in a rigid clamping means and ultrasonically vibrating the file in a transverse, wave-like motion to enhance the debriding action. It is also known to provide an irrigating fluid directed from an ultrasonically vibrating endodontic file longitudinally of the axis of the file to enable irrigation of the root canal while the debriding action is proceeding; however, the known ultrasonically vibrated endodontic file supports and root canal irrigating devices have not generally been capable of selectively separately and controllably applying fluid medication or other irrigating liquid other than the cooling liquid circulated through the dental handpiece. Further, effective use of the cooling and vibration isolating liquid in the handpiece requires a substantially continuous flow of cooling liquid which may be substantially greater than the flow rate necessary or desired in irrigating a root canal. Accordingly, it is the primary object of the present invention to provide an improved ultrasonically vibrated endodontic instrument which overcomes the above and other defects of the prior art.

SUMMARY OF THE INVENTION

Another object of the invention is to provide an improved endodontic file holder adapted to be inserted in and used with known prior art ultrasonic handpieces whereby known ultrasonic dental handpieces may be adapted for endodontic use.

Another object is to provide an universal endodontic file holder for use with an ultrasonic dental handpiece of the type employing a circulating cooling fluid and providing means for continuing circulation of the cooling fluid through the handpiece and for selectively discharging a second fluid from the file holder along the axis of the file to irrigate a root canal during use.

Another object of the invention is to provide an improved fluid dispensing apparatus for use in connection with an ultrasonic endodontic instrument to enable a controlled selective delivery of an irrigating fluid longitudinally of the endodontic instrument during use.

In the attainment of the foregoing and other objects and advantages, an important feature of the present invention resides in providing a fluid dispensing insert assembly for use in connection with an ultrasonic dental handpiece and which includes means for rigidly supporting an endodontic instrument such as a root canal file in position to impart transverse wave ultrasonic vibrations in the instrument while efficiently transfering the ultrasonic energy to the instrument. The insert assembly includes a rigid metal body element having a longitudinally extending bore for delivering irrigating fluid for discharge from the body head adjacent to and in a direction parallel with the root canal file. External fluid supply conduit means is provided for delivering irrigating fluid to the insert assembly through a lateral bore in the rigid body, and means are provided for sealing the irrigating fluid flow path to exclude any cooling fluid flowing in the handpiece. A separate external flow path is provided for the return of any cooling fluid in the handpiece whereby cooling fluid may be employed in the normal manner without requiring the fluid to be discharged from the end of the handpiece and without requiring any modification to the ultrasonic handpiece.

Fluid dispensing apparatus connected with the dispensing insert assembly is operable to provide a controlled flow of irrigating fluid which may contain medicaments or the like, the use of which may not be desired on a continuous or uncontrolled basis. Further, even when water or other inert or inactive irrigating fluid is employed, it is desired to be able both to control the flow rate during irrigation and to stop the flow of irrigating fluid during portions of the procedure. This may be accomplished in accordance with the present invention by use of a multiposition foot-actuated switch wherein in the fully raised or unactuated position, power to the instrument is off and both cooling fluid to the handpiece and irrigating fluid from the dispensing mechanism are off. In the second or intermediate position of the switch, the ultrasonic handpiece is energized and the cooling fluid is circulated through the handpiece and returned externally of the handpiece through the return line, but the irrigating fluid dispensing mechanism is not actuated and no irrigating fluid flows from the apparatus. In the third or fully depressed position of the switch, power and cooling fluid continue to be supplied to the dental handpiece in the manner described, and the irrigating fluid dispensing mechanism is actuated to provide a controlled flow of irrigating fluid through the dispensing insert assembly for discharge along the root canal file axis. The irrigating fluid dispensing mechanism preferably includes adjustable means for accurately controlling the rate of flow therefrom.

Upon completion of the endodontic procedure, the dispensing insert assembly may be simply removed from the dental handpiece and another insert assembly such as a cleaning head inserted to enable the handpiece to be used for other procedures so that maximum utilization of the ultrasonic equipment is achieved.

BRIEF DESCRIPTION OF THE DRAWINGS

Other objects and advantages of the invention will be apparent from the detailed description contained hereinbelow, taken in conjunction with the drawings, in which.

DETAILED DESCRIPTION OF THE PREFERRED EMBODIMENTS

Ultrasonic cleaning instruments are well-known and widely used in the dental art and numerous commercial devices are available for accomplishing various procedures and to satisfy the desires or preferences of the individual. The present invention is particularly well adapted for but not limited to use with the ultrasonic dental cleaning device of the type disclosed and described in the above-mentioned reissue patent which incorporates means for flowing a liquid through the handpiece to cool the electrically excited ultrasonic device. This cooling liquid, typically water, flows through the handpiece and is discharged from the end of the device in the direction of the operative tip of the instrument. While operation of the ultrasonic cleaning device is described in detail in U.S. Pat. No. Re. 30,536, the basic structure will be briefly described here to facilitate understanding of the present invention. Also, while the entire assembly illustrated in FIG. 1 is sometimes referred to generally as a handpiece, this term is used herein to refer only to the rigid housing and electrical components at the aft section of the instrument whereas the removable portion at the forward or working end of the apparatus will be referred to as an insert assembly, or a dispensing insert assembly.

Figure 1:
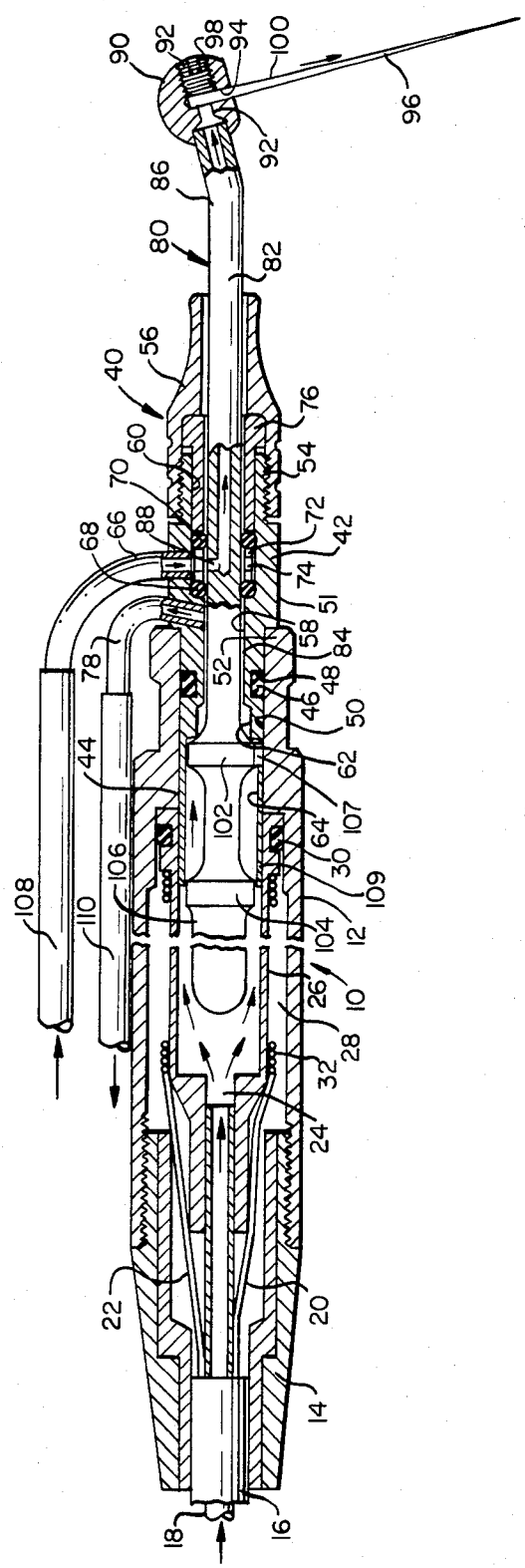
FIG. 1 is a longitudinal sectional view of an ultrasonic device incorporating the improved dispensing insert assembly of the present invention.

The ultrasonic handpiece is indicated generally in FIG. 1 by the reference numeral 10 and includes an outer, substantially cylindrical tubular housing 12 closed at its aft end by a threaded end cap member 14. A compound cable assembly 16 is mounted in and extends through end cap 14 and contains a central, flexible hose 18 and a pair of electrical conductors or wires 20, 22.

The flexible hose 18 extends into and forms a fluid-tight seal with an axial opening 24 in the end of an internal housing member 26 which is mounted coaxially within and in inwardly spaced relation to the inner surface of housing 12 to define an annular space 28. An O-ring seal 30 on the forward end of inner housing 26 cooperates with the inner surface of outer housing 12 to form a fluid-tight seal adjacent the forward end of the handpiece. Conductors 20, 22 are connected to the windings of a coil, indicated generally at 32, wound on the outer surface of inner housing 26 so that, when the conductors 20, 22 are connected to a suitable power source externally of the handpiece, a high frequency alternating electromagnetic field is established. The forward end of the outer housing 12 has a reduced diameter bore corresponding to the internal diameter of inner housing 26, with the two surfaces being adapted to telescopingly receive and support a cylindrical surface on a separable, cooperating insert assembly 40, with the insert assembly being retained by friction only to enable easy separation and replacement with another insert assembly.

Referring to the forward, or operative end of the apparatus, i.e., the end at the right in FIG. 1, the removable dispensing insert assembly 40 comprises an elongated rigid body member 42 including a central section 44 with a cylindrical outer surface substantially equal to the diameter of the inner surface of inner housing member 26 and the forward end of outer housing member 12. An O-ring seal 46 mounted within an O-ring groove 48 frictionally engages the inner surface 50 of housing 12 to provide a fluid-tight seal between body 42 and the outer housing 12 and to resiliently retain the body within the housing. The forward portion 51 of body 42 is of enlarged diameter and provides a shoulder 52 adapted to engage the forward end of outer housing 12 to accurately position the insert within the handpiece. The forward section 54 of body 42 is threaded on its outer surface to threadably engage and support an internally threaded nut member 56. A small diameter bore 58 extends axially through body 42, and a counterbore 60 extends into the body member from its forward end to a position within the enlarged forward section 51. Also, first and second counterbores formed in the rear end of the body 42 provide first and second cylindrical surfaces 62, 64.

A rigid tubular elbow member 66 has one end mounted in a radial bore in the enlarged central section 51 of body 42, with the tubular member preferably being secured by brazing or welding to provide a rigid watertight seal. A pair of O-rings 68, 70 mounted within the counterbore 60 retain an annular spacer sleeve 72, and radially extending openings 74 formed in the spacer sleeve permit the flow of liquid from tubular member 66 through the spacer member. A retaining sleeve 76 is telescopingly received in the forward end of body 42 to position the O-rings 68, 70 and spacer sleeve 72, with the sleeve 76 being held in position by the threaded nut 56.

A second rigid curved tubular member 78 is secured, as by brazing, in a second generally radially extending bore in the enlarged section of body 42 and provides fluid communication with the small diameter bore section 58 at a location rearward from the O-ring seal 68. The purpose for this second tubular member will be described more fully hereinbelow.

An elongated tool support assembly 80 is slidably supported within body member 42 and includes rigid shank portion 82 having an external diameter slidably less than the diameter of bore 58 to provide an annular fluid flow passage 84 therebetween. An axial bore 86 is formed in the outwardly projecting end of shank 82, with the bore 86 terminating at a location between the O-rings 68 and 70. A radial bore 88 provides a fluid flow path from tubular member 66 and the openings 74 in spacer member 72 into the bore 86. An enlarged head member 90 is rigidly mounted, as by brazing or welding, on the distal end of shank 82 and a bore 92 extends through the rigid head to communicate with the bore 86 in shank 82. A radially extending bore 94 is also formed in head 90, with bore 94 extending transversely of bore 92 to receive the support butt end of a replaceable root canal file 96. A sealing and locking set screw 98 mounted in a threaded counterbore in head 90 is adapted to engage and firmly retain the butt of the root canal file seated in the head. The diameter of the bore 94 is larger than the diameter of bore 92 so that fluid flowing through the shank portion member 82 can flow around the end of the root canal file and be discharged from the head 90 axially along the root canal file in the direction indicated by arrows 100.

The tool support assembly 80 has a connecting body portion disposed within the aft end of body 42, with the connecting body including a pair of enlarged sections 102, 104 each having a diameter slightly less than the diameter of the cylindrical surface 64. A key 107 integrally formed on the cylindrical connecting body portion 102 is disposed with an elongated slot 109 in the wall of body member 42 to prevent rotation of the tool support assembly within the body member.

A body of magnetostrictive material is rigidly mounted, as by brazing or welding, on the aft end of the connecting body portion of the tool support assembly and is excited in the longitudinal direction by the high frequency field established by the coil 32 to impart the desired longitudinal vibrations to the tool support assembly. These vibrations are transmitted in the conventional manner through the rigid metal of the shank 82 and imparted to the root canal file 96 in a direction substantially transversely of its longitudinal axis to establish a standing wave-like vibration pattern to the file which is highly effective in debriding a root canal. At the same time, fluid under pressure admitted through the flexible tube 108 can flow through connecting tube 66 into the bore 60 of body member 42 and, being restricted by the O-ring 68 and 70, is confined to flow through the radial bore 88 and axial bore 86 to the vibrating head 90 to be discharged along the surface of the root canal file 96.

Cooling water admitted to the handpiece through flexible tube 18 is permitted to flow through the handpiece within the inner housing 26 and over the surface of the magnetostricitve material 106 and connecting body portions 102, 104 to the annular space 84. The O-ring 68 blocks flow of cooling fluid beyond this point, forcing it to flow out through outlet tube 78. A flexible tube 110 is connected to the tubular member 78 to provide an escape for the cooling fluid which would normally be from the end of the insert assembly when the handpiece is used in connection with a cleaning tool or the like. Thus, the dispensing insert assembly described enables the flow of cooling fluid through the handpiece while at the same time providing a flow path for an irrigation fluid which flow path is completely isolated from the cooling fluid. Tube 110 can be led to a suitable drain, sump, or the like since water as from a conventional municipal water supply system is normally employed as the cooling water.

The rigid mounting structure provided for the root canal file substantially reduces fatigue failures and fluid leaks, thereby providing efficient transfer of vibration energy to the working instrument which is another important feature of the invention.

Figure 2:
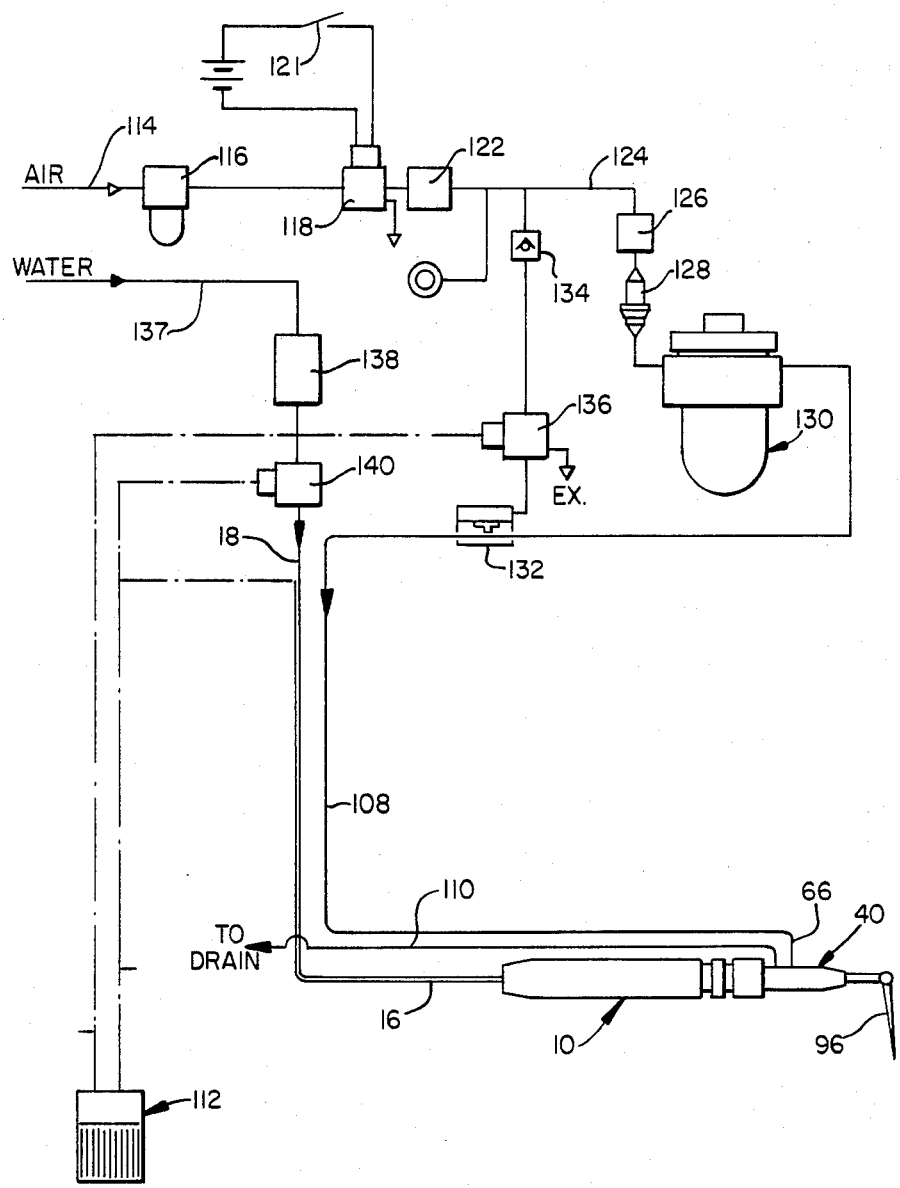
FIG. 2 is a schematic view of the ultrasonic endodontic apparatus and control system according to the present invention.

Referring now to FIG. 2 the ultrasonic endodontic apparatus previously described is schematically illustrated as connected in a control system including a three-position foot actuated control switch 112 selectively operable to control the flow of cooling water and power to the handpiece and the flow of an irrigating fluid to the dispensing insert assembly. Air, under pressure, is supplied through line 114 from a suitable compressed air source such as a conventional dental office air supply compressor, not shown. The air from line 114 passes initially through an inlet, or preliminary filter 116 then through a main solenoid-actuated shut-off valve 118 connected, through lines 120 and main control switch 121 to a suitable power source.

From shut-off valve 118, the air flows through a first pressure reducer 122 then through line 124 to a second pressure reducer 126 and a one-way check valve 128 to be discharged into an irrigation fluid dispensing assembly 130. Air admitted into the dispensing assembly 130 pressurizes the irrigation fluid, causing it to flow through line 108 and connecting tube 66 to the dispensing insert assembly 40. Flow through line 108 is controlled by an air pressure actuated pinch-type shut-off valve 132 connected to line 124 through a one-way check valve 134 and solenoid actuated valve 136. Valve 136 is connected to contacts within foot-actuated switch 112 to be energized open when the switch 112 is moved to its third, fully depressed position. Pinch valve 132 is preferably a normally open air energized diaphragm-actuated pinch valve which is closed only when air pressure is admitted to the valve by de-energizing solenoid valve 136 to the open position.

Cooling water is supplied to handpiece 10 from a suitable source through line 137 connected to pressure regulator 138 and solenoid actuated valve 140 which in turn is connected to the flexible tube 18. Solenoid valve 140 is connected to contacts within foot-actuated switch 112 to be energized when the switch is depressed to its second or intermediate position. At the same time, power is supplied to the coil 32 through the conductors 20, 22. Thus, when the switch 112 is in its first or unactuated position, solenoid valves 140 and 136 are de-energized so that water will not flow through tube 18 and pinch valve 132 will prevent the flow of irrigation fluid through line 108. If solenoid valve 118 is energized open, air flowing through line 124 will be admitted in the irrigation fluid dispenser assembly 130 so that the dispenser remains pressurized; however, no fluid can be dispensed since pinch valve 132 is closed. When switch 112 is depressed to its second position, power will be supplied to the coil 32 within handpiece 10 and to valve 140 to admit the flow of cooling water through the handpiece and out through line 110 into a suitable drain. Under these conditions, no irrigation fluid will flow through line 108, but the dental file 96 will be excited by the ultrasonic vibrations of the apparatus in the manner described hereinabove. Upon movement of switch 112 to its third or fully depressed position, power will continue to be supplied to coil 32 and valve 140 and will also be supplied to close valve 136 and exhaust air pressure necessary to open pinch valve 132 and permit irrigation fluid to flow to the dispensing insert assembly.

Figure 3:
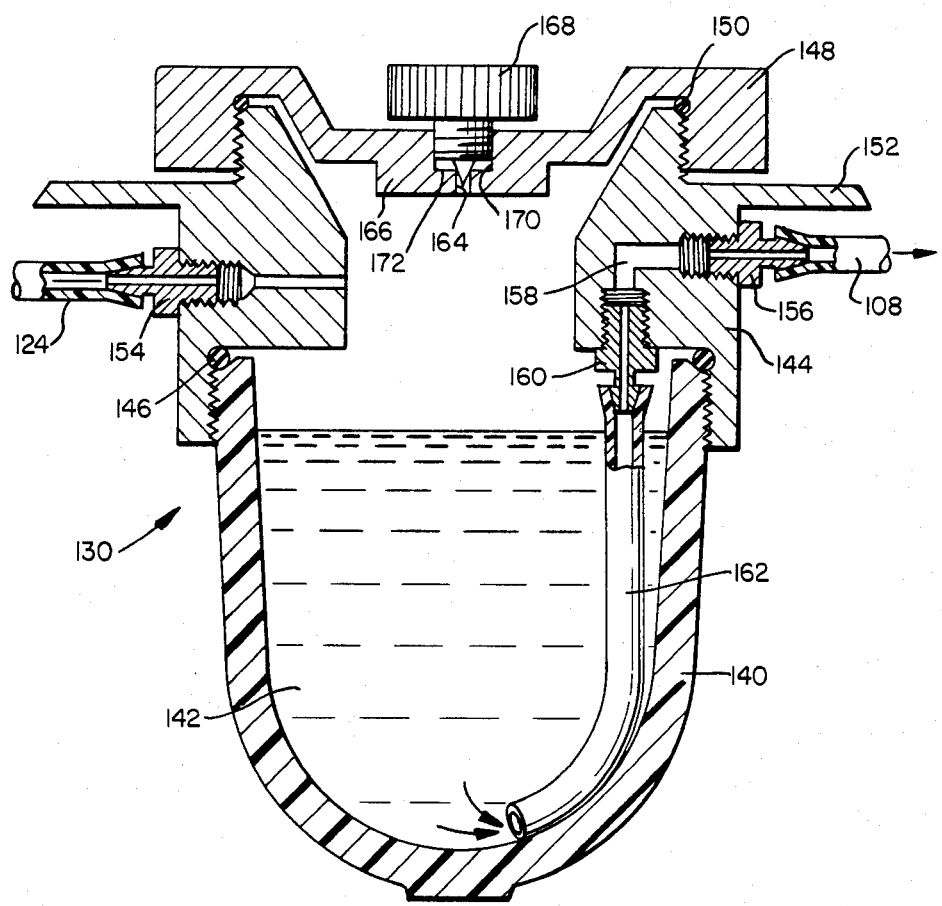
FIG. 3 is a sectional view of the irrigation fluid dispensing mechanism employed in the invention.

Referring now to FIG. 3, the irrigation fluid dispensing assembly 130 comprises a bowl 140 for containing a supply of irrigation fluid indicated generally at 142. Bowl 140 is preferably formed from a high strength transparent or translucent material to permit viewing of the contents, with the material being capable of withstanding cleaning in suitable sterilizing solutions. The bowl has an open top threaded into and supported by a rigid housing 144, and a resilient O-ring 146 provides a fluid-tight seal between the housing and bowl. A threaded cap, or closure member 148 is mounted on the top of housing 144 and a removable O-ring 150 forms a seal between the closure and housing. A flange 152 is provided on housing 144 to enable mounting the assembly on the top panel of suitable cabinet structure, with the closure 14 8 projecting above the closure to facilitate filling of the bowl 140 and to provide access for the flow regulating means described more fully hereinbelow.

Air, under carefully regulated pressure, is supplied through conduit 124 attached to an inlet fitting 154 in housing 144 to pressurize the body of irrigation liquid 142 in the bowl. Irrigation liquid delivery tube 108 is connected to an outlet fitting 156 mounted in communication with a drilled passage 158 in housing 144, and a second fitting 160 is mounted on housing 144 in communication with the passage 158 on the interior of the dispensing assembly chamber. A short length of flexible tubing 162 is frictionally supported on the fitting 160 and extends downwardly to terminate in an open end adjacent the bottom of the bowl 140. Thus, it is seen that air pressure admitted through tube 124 will pressurize the interior of the dispensing assembly, tending to cause the fluid to flow out through tube 162 into irrigation supply tube 108, with this flow being controlled by the pinch valve 132.

The maximum pressure within the irrigation dispensing assembly chamber is limited by the pressure regulator 126, with this maximum pressure normally being maintained relatively low to avoid possible discomfort to the patient and excessive spray or splash back when the fluid is discharged along the root canal file. Flow rates below the maximum determined by the pressure regulator 126 may be regulated by a flow adjustment feature in the closure cap 148. This flow regulator comprises a bleed-off outlet 164 formed in a recessed center panel portion 166 of closure 148. A flow control adjuster 168 is threadably mounted in a threaded counterbore 170 in the closure cap, with a needle valve tip 172 projecting into bleed-off outlet 164. Thus, a portion of the air admitted into the supply chamber can be bled off to thereby reduce the pressure in the chamber and consequently the flow rate of irrigation fluid through tube 108.

Preferably the flow control adjustment includes a relief either in the outlet 164 or in the needle valve portion 172 to prevent complete sealing of the bleed-off outlet. This safety feature assures that air pressure in the chamber will be bled off when the system is shut down, thereby avoiding the possibility of the closure 148 or the bowl 140 being removed while the system is pressurized.

Experimentation has determined that a maximum pressure within the irrigating fluid supply chamber of about 8 to 10 psi is adequate and that a preferred pressure may be within the range of about 5 to 8 psi. Since the flow rates through the small diameter tubing and channels of the entire system are inherently low, only a relatively small volume of air needs to be bled off through the outlet 164 to reduce the maximum air pressure within the chamber to the desired level. Thus excess energy is not wasted by bleeding off the compressed air and the flow rate of bleed-off air is sufficiently low as to avoid objectionable noise. By mounting the flow rate adjustment knob 168 within the recess portion of the closure cap, it is readily accessible but is protected against inadvertent changes.

The irrigation fluid dispensing apparatus described above enables controlled dispensing relatively low volumes of low pressure irrigation fluid as desired by the operating dentist. Since the fluid is used only for irrigation purposes and only as required, medications, sterilizing solutions and the like can be included in the irrigating fluid so that the dentist does not have to interrupt the debriding procedure for the application of medicaments or for irrigating the root canal.

It should be apparent that various modifications may be made to the invention as described. Accordingly, while a preferred embodiment of the invention has been disclosed and described, it should be understood that it is not intended to be so limited but rather it is intended to include all embodiments which would be apparent to one skilled in the art and which come within the spirit and scope of the invention.

What is claimed is:

1. In an ultrasonic device including a handpiece having an elongated hollow housing, coil means in said housing adapted to be connected to an external energy source for establishing an alternating electromagnetic field within said housing, said housing having a cooling fluid inlet at one end and being open at its other end, and an insert adapted to be removably mounted on the other end of said handpiece, said insert comprising, an elongated hollow body having one end adapted to be insertably mounted in said open end of said housing with said one end of said body being in fluid communication with the interior of the housing whereby cooling fluid admitted into said housing can flow into said body, a tool support assembly telescopingly received in said body, said tool support assembly including an elongated shank having vibrating means rigidly mounted on one end, said vibrating means projecting from the open end of the said body in position to be vibrated by the electromagnetic field when said body is mounted in said housing, seal means provided within said insert between said body and said shank outboard of said housing for directing the flow of cooling fluid through said body between said seal means, cooling fluid outlet means in said body between said seal means and said one end of said body providing a flow path for cooling fluid from said handpiece, the other end of said shank projecting outward from said body and terminating in mounting means for supporting an endodontic instrument, said shank having a fluid flow passage extending longitudinally therein from said mounting means and terminating at a location within said body, and irrigation fluid inlet means for admitting an irrigation fluid into said fluid flow passage to be discharged from said mounting means in a direction substantially parallel to the endodontic instrument mounted in said mounting means, whereby said irrigation fluid and said cooling fluid may be separately controlled.

2. In the ultrasonic device defined in claim 1, the further improvement wherein said irrigation fluid inlet means comprises a radially extending bore in said shank, an inlet opening in said body for admitting irrigation fluid between said body and said shank, said seal means between said shank and said body providing a sealed flow path between said inlet opening and said radially extending bore.

3. The ultrasonic device defined in claim 2, further comprising means on said tool support assembly engaging said body to prevent relative rotation therebetween.

4. The ultrasonic device defined in claim 2, wherein said mounting means comprises an enlarged head rigidly mounted on said other end of said shank, a first bore extending through said head and substantially aligned with said fluid flow passage in said shank, a second bore extending into said head and intersecting said first bore, said second bore being adapted to receive the shank end of a endodontic instrument and having a diameter larger than the endodontic instrument, and threaded fastener means for rigidly clamping an endodontic instrument in said second bore.

5. The ultrasonic device defined in claim 4 wherein the diameter of said first and second bores in said head are each larger than the endodontic instrument to be supported whereby irrigation fluid can flow from the head axially along the endodontic instrument.

6. The ultrasonic device defined in claim 5 wherein said seal means comprise a pair of O-ring seals disposed one on each side of said inlet means and said radially extending bore.

7. The ultrasonic device defined in claim 6 further comprising conduit means connected with said outlet means for conducting cooling water from said handpiece.

8. The ultrasonic device defined in claim 1 further comprising dispensing means including a closed chamber for containing a volume of irrigation liquid, conduit means connecting said closed chamber to said irrigation fluid inlet means, selectively operable valve means connected in said conduit means for controlling the flow therethrough, and means directing air under pressure into said closed chamber to cause irrigation fluid contained therein to flow through said conduit means when said valve means is open.

9. The ultrasonic device defined in claim 8 further comprising bleed-off means in said closed chamber, said bleed-off means being operable to control the air pressure in the chamber.

10. In the ultrasonic device defined in claim 7 the further improvement wherein said irrigation fluid inlet means comprises a radially extending bore in said shank, an inlet opening in said body for admitting irrigation fluid between said body and said shank, said seal means between said shank and said body providing a sealed flow path between said inlet opening and said radially extending bore.

11. The ultrasonic device defined in claim 10, further comprising means on said tool support assembly engaging said body to prevent relative rotation therebetween.

12. The ultrasonic device defined in claim 11, wherein said mounting means comprises an enlarged head rigidly mounted on said other end of said shank, a first bore extending through said head and substantially aligned with said fluid flow passage in said shank, a second bore extending into said head and intersecting said first bore, said second bore being adapted to receive th shank end of a endodontic instrument and having a diamter larger than the endodontic instrument, and threaded fastener means for rigidly clamping an endodontic instrument in said second bore.

13. The ultrasonic device defined in claim 12 wherein the diameter of said first and second bores in said head are each larger than the endodontic instrument to be supported whereby irrigation fluid can flow from the head axially along the endodontic instrument.

14. The ultrasonic device defined in claim 13 wherein said seal means comprise a pair of O-ring seals disposed one on each side of said inlet means and said radially extending bore.

* * * * *